United States Patent
Axelson, Jr.

(10) Patent No.: US 8,449,547 B2
(45) Date of Patent: May 28, 2013

(54) CUTTING BLOCK FOR BONE RESECTION

(75) Inventor: Stuart L. Axelson, Jr., Succasunna, NJ (US)

(73) Assignee: Howmedica Osteonics Corp., Mahwah, NJ (US)

( * ) Notice: Subject to any disclaimer, the term of this patent is extended or adjusted under 35 U.S.C. 154(b) by 610 days.

(21) Appl. No.: 12/611,489

(22) Filed: Nov. 3, 2009

(65) Prior Publication Data

US 2010/0057089 A1    Mar. 4, 2010

Related U.S. Application Data

(62) Division of application No. 11/472,610, filed on Jun. 22, 2006, now abandoned.

(51) Int. Cl.
*A61B 17/58*    (2006.01)

(52) U.S. Cl.
USPC .............................................. 606/86; 606/87

(58) Field of Classification Search
USPC ............... 606/86 R–90, 96–98, 102
See application file for complete search history.

(56) References Cited

U.S. PATENT DOCUMENTS

| | | | |
|---|---|---|---|
| 4,567,885 A | 2/1986 | Androphy | |
| 4,938,762 A | 7/1990 | Wehrli | |
| 5,122,144 A | 6/1992 | Bert et al. | |
| 5,540,695 A | 7/1996 | Levy | |
| 5,611,353 A | 3/1997 | Dance et al. | |
| 5,643,272 A | 7/1997 | Haines et al. | |
| 5,957,926 A | 9/1999 | Masini | |
| 6,385,475 B1 | 5/2002 | Cinquin et al. | |
| 6,458,135 B1 | 10/2002 | Harwin et al. | |
| 6,514,259 B2 | 2/2003 | Picard et al. | |
| 2002/0091403 A1 | 7/2002 | Bonutti | |
| 2002/0107522 A1 | 8/2002 | Picard et al. | |
| 2002/0133163 A1 | 9/2002 | Axelson et al. | |
| 2002/0198451 A1 | 12/2002 | Carson | |
| 2002/0198531 A1 | 12/2002 | Millard et al. | |
| 2003/0018338 A1 | 1/2003 | Axelson et al. | |
| 2003/0069585 A1 | 4/2003 | Axelson et al. | |
| 2003/0069591 A1 | 4/2003 | Carson et al. | |
| 2003/0171757 A1 | 9/2003 | Coon et al. | |
| 2003/0181984 A1 | 9/2003 | Abendschein | |
| 2003/0212403 A1* | 11/2003 | Swanson | 606/88 |
| 2004/0039396 A1 | 2/2004 | Couture et al. | |
| 2004/0138670 A1* | 7/2004 | Metzger | 606/88 |
| 2005/0055028 A1 | 3/2005 | Haines | |
| 2005/0102032 A1 | 5/2005 | Beynnon et al. | |

(Continued)

OTHER PUBLICATIONS

Howmedica, Inc., Catalogs, p. B-24, 1978.

*Primary Examiner* — Kevin T Truong
*Assistant Examiner* — Michael T Schaper
(74) *Attorney, Agent, or Firm* — Lerner, David, Littenberg, Krumholz & Mentlik, LLP

(57) ABSTRACT

A cutting block having a base, and a top connected to the base via four walls is disclosed. Each wall has an outwardly facing surface to guide a cutting tool. Each wall also has an attachment hole where a tracker may be attached. The cutting block is floated on the bone using the navigation system to position it at correct locations for the bone resection. After correctly locating the cutting block for each required cut, cutting block is fixed to the bone using pins and the bone resected. Same cutting block is suitable for resection of bone for installation of any size prosthetic device. For certain resections, the rotation angle may be mechanically set and need not be navigated.

7 Claims, 8 Drawing Sheets

U.S. PATENT DOCUMENTS

| | | |
|---|---|---|
| 2005/0113840 A1* | 5/2005 | Metzger et al. .................. 606/88 |
| 2005/0171545 A1 | 8/2005 | Walsh et al. |
| 2005/0203531 A1* | 9/2005 | Lakin et al. .................... 606/87 |
| 2005/0209605 A1 | 9/2005 | Grimm et al. |
| 2005/0240195 A1* | 10/2005 | Axelson et al. ................. 606/87 |
| 2005/0261697 A1 | 11/2005 | Canonaco et al. |
| 2006/0122617 A1 | 6/2006 | Lavallee et al. |
| 2006/0293681 A1* | 12/2006 | Claypool et al. ................ 606/87 |

* cited by examiner

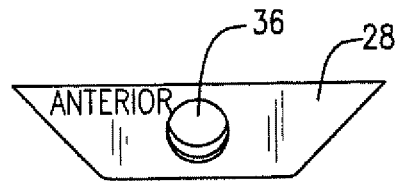
FIG. 5
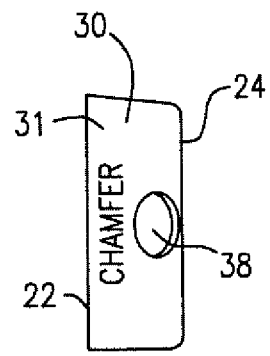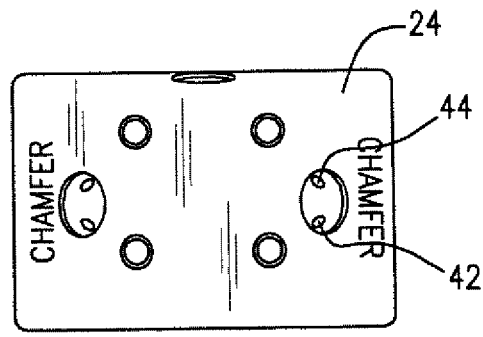
FIG. 6     FIG. 3
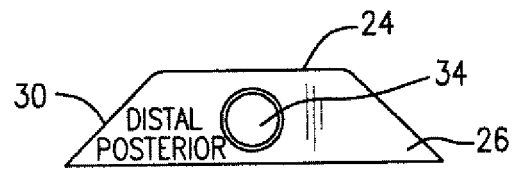
FIG. 4
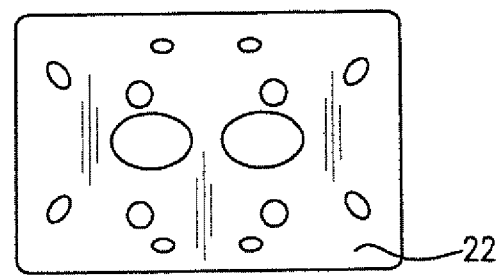
FIG. 7

CUTTING BLOCK FOR BONE RESECTION

CROSS-REFERENCE TO RELATED APPLICATIONS

This application is a divisional of U.S. application Ser. No. 11/472,610, filed on Jun. 22, 2006 the disclosure of which is incorporated herein by reference.

BACKGROUND OF THE INVENTION

This invention relates to method and apparatus for resecting a bone. In particular this invention relates to a method and apparatus for performing all of the bone resections required for implanting a prosthesis using one bone resection instrument such as a cutting block. More particularly, this invention relates to a navigated cutting block that can be "floated" around the bone to be resected to set up the planes for resection.

There are several types of prostheses known in the art. One type is sometimes referred to as a "resurfacing type". In these prostheses, the articular surfaces of the bones are "resurfaced" with articular bearing components. One important aspect of these procedures is the correct resection of the bones. These resections must provide planes which are correctly angled in order to properly accept the prosthetic components.

Recently, various computerized navigation systems have been introduced to aid the practitioner during different surgical procedures. These systems include multiple video cameras which are deployed above the surgical site and a plurality of dynamic reference frame (DRF) devices, also known as trackers, which are attached to body parts and surgical instruments. The trackers can be LED devices or reflective spheres which are visible to the cameras. These trackers are attached to body parts and the surgical instruments and preferably include light emitting devices, such as light emitting diodes which are visible to the video cameras. The trackers communicate position information to a camera system located in the operating room. The camera system is connected to a computer which tracks the location of the tracker and the patient and displays the relationship on a CRT. Using software designed for a particular surgical procedure, a computer receiving input from the cameras guides the placement of surgical instruments such as cutting blocks for bone resection.

The prior art cutting blocks have several shortcomings. In case of a total knee arthroplasty that involves the replacement of portions of the patella, femur and tibia with artificial components, separate distal resection block and a block for making remaining resections on the femur are required. Also, different size resection blocks are required for different size implants. This increases the inventory of parts in the operating room. Additionally the prior art cutting blocks are sized in proportion to the size of the implant and are not very suitable for minimally invasive surgery. Therefore, there is a need for a navigable cutting block that is small in size, suitable for use with all sizes of implants and allows for all the necessary resections using a single cutting block.

As used herein, when referring to bones or other parts of the body, the term "proximal" means closer to the heart and the term "distal" means more distant from the heart. The term "inferior" means toward the feet and the term "superior" means towards the head. The term "anterior" means towards the front part of the body or the face and the term "posterior" means towards the back of the body. The term "medial" means toward the midline of the body and the term "lateral" means away from the midline of the body.

SUMMARY OF THE INVENTION

Cutting blocks of the present invention overcome the shortcomings of the prior art and provide a single cutting block that can make all the resections on a bone (e.g., a femur), is small in size and is suitable for use with all sizes of the implants.

A first embodiment of the cutting block of the present invention has a base, and a top connected to the base via four walls. Each wall (i.e., the cutting guide) has an outwardly facing surface to guide a cutting tool. Each wall also has an attachment hole where a tracker may be attached. The cutting block is floated, on the bone, free hand by the surgeon using the navigation system to position it at correct locations for the bone resection. After correctly locating the cutting block for each required cut, the cutting block is fixed to the bone using pins and the bone resected.

A second embodiment of the cutting block has a base, and a top connected to the base via four walls. Three of the four walls have outwardly facing surfaces that are used to guide a cutting tool. Each one of these outwardly facing surface has an attachment hole where a tracker may be attached. The cutting block is floated free hand by the surgeon on the bone using the navigation system to position it at correct locations for the bone resection. After correctly locating the cutting block for each required cut, the cutting block is fixed to the bone by inserting pins through the holes in the cutting block and in the bone. Next, the bone is resected. In this embodiment only three outwardly facing surfaces are used to guide a cutting tool, however, the surfaces may be used to guide the cutting tool in making more than one cuts on the bone.

In yet another embodiment, the cutting block has two pairs of slots in addition to features of the second embodiment. Once the block is first attached to the distal end of the femur, the pins that attached the block to the distal end are left in place and the block relocated to make additional cuts on the bone by sliding the pins in one of the two pairs of slots. Since the block is now partially located by the pins, the rotation of the remaining resection is mechanically set and need not be navigated. The second set of slots is similarly used to make other resections.

In use the cutting blocks described above are floated on the anterior surface of the bone to be resected, fixed in the correct location and one of the outwardly facing surfaces used to make the distal cut on the bone. Thereafter, the cutting block is floated on the resected distal end of the bone and fixed in the correct location for making another cut. The process is repeated to as many times as necessary. In one embodiment the cutting blocks rotational position is mechanically set as described previously.

BRIEF DESCRIPTION OF THE DRAWINGS

FIG. 3 is a plan view of the cutting block of FIG. 1.

FIGS. 4, 5 and 6 are side views from different sides of the cutting block of FIG. 1.

FIG. 7 is another plan view showing the base of the cutting block of FIG. 1.

DETAILED DESCRIPTION

Figure 1:
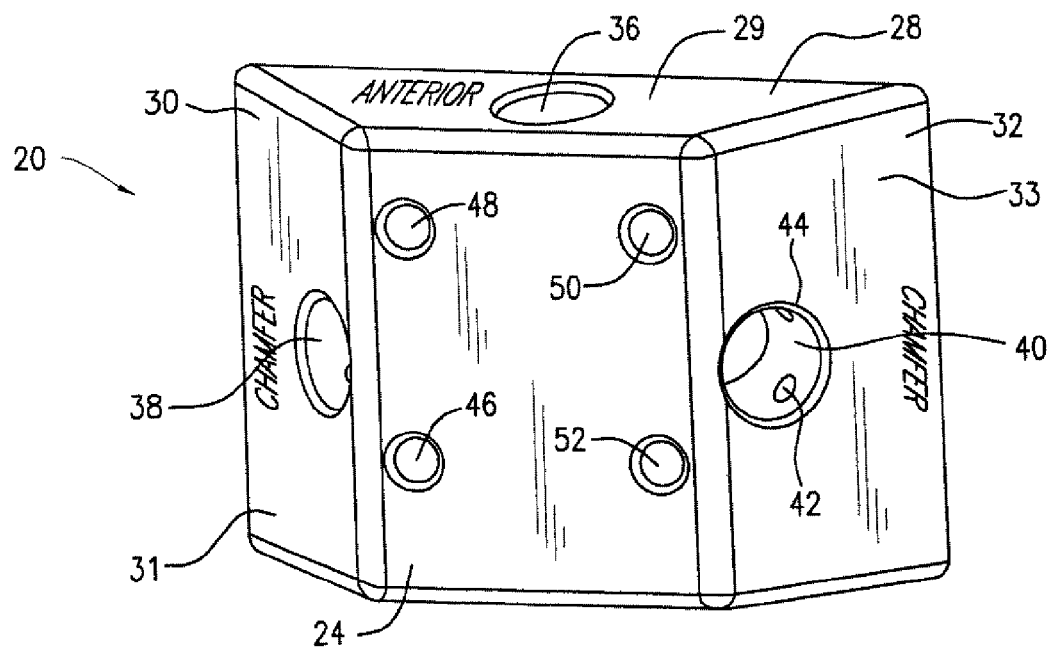
FIG. 1 is an isometric view of a cutting block.
Figure 2:
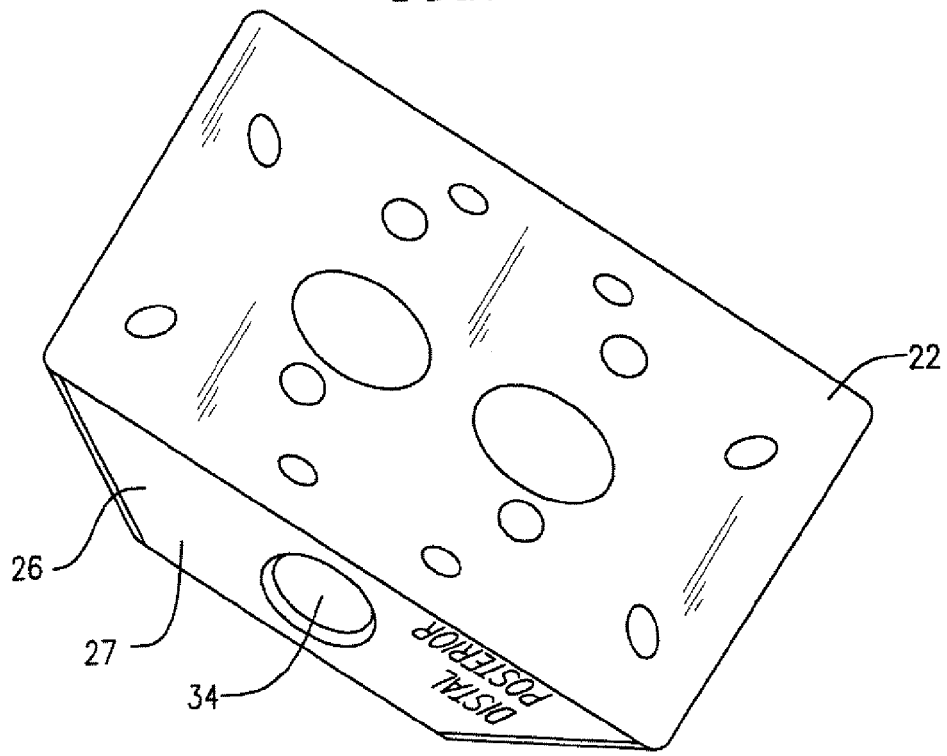
FIG. 2 is an isometric view of the cutting block of FIG. 1 from a different angle.

FIGS. 1-7 show a first embodiment of a cutting block 20. Cutting block 20 has a base 22 and a top 24. Base 22 is connected to top 24 via four walls 26, 28, 30 and 32. Wall 28 runs from base 22 to top 24 and has an outwardly facing surface 29 to guide a cutting tool. Surface 29 of wall 28 may be angled to match an angle on prosthesis such as a femoral prosthesis. The angle may be, for example, seven degrees with respect to base 22. The outwardly facing surface 29 may be used to make, for example, an anterior cut on a femur. Wall 26 runs from base 22 to top 24 and has an outwardly facing surface 27 to guide a cutting tool. Outwardly facing surface 27 of wall 26 may be used, for example, to make distal and posterior cuts on a femur. Wall 30 runs from base 22 to top 24 and has yet another outwardly facing surface 31 that may guide a cutting tool. Wall 30 may be angled with respect to base 22. The angle that wall 30 forms with base 22 may be determined based upon the angle at which certain cut, for example, a chamfer cut on a femur is to be made. Wall 32 runs from base 22 to top 24 and has yet another outwardly facing surface 33 that may guide a cutting tool. Wall 32 may also be angled with respect to base 22. The angle that wall 32 forms with base 22 may also be determined based upon the angle that a certain cut, for example, a chamfer cut on a femur is to be made. The angles made by walls 30 and 32 with base 22 may be same or may differ from each other. Cutting block 20 may be formed, for example, from a solid or hollow piece of metal, plastic or other suitable material and provide the outwardly facing surfaces described above and other features that will be described hereafter.

Walls 26, 28, 30, 32 have attachment holes 34, 36, 38 and 40 respectively. A tracker may be attached to any one of the attachment holes 34, 36, 38 and 40, for navigating cutting block 20 for proper positioning on the corresponding surface on the bone. Holes 34, 36, 38 and 40 each have small openings 42 and 44 seen in FIGS. 1 and 3. Openings 42 and 44 accommodate spring loaded ball like structures on the tracker attached in any one of the holes 34, 36, 38 and 40, thereby aiding in attachment of tracker to cutting block 20. Top 24 has four holes 46, 48, 50 and 52. A pin may be driven through one or more of holes 46, 48, 50 and 52 to attach cutting block 20 to a bone. Top 24 may have more or less than four holes.

FIGS. 8-14 show a cutting block 54 that is a second embodiment of the invention. If the chamfer cuts on a bone are to be at same angle, cutting block 20 can be made smaller. Cutting block 54 is an example of such smaller block that is more suitable for minimally invasive surgery. Cutting block 54 has a base 56 and a top 58. Walls 60, 62, 64 and 66 run from base 56 to top 58. Wall 62 has an outwardly facing surface 63 which may guide a cutting tool. Wall 62 may be angled, for example, seven degrees with respect to the base, to match the angle on the prosthesis to be used. Wall 64 has an outwardly facing surface 65 to guide a cutting tool. Wall 64 is angled with respect to the base. The angle is determined based upon the angle that a certain cut, for example, a chamfer cut on a femur is to be made. Outwardly facing surface 65 may also be used to make another cut, for example, a second chamfer cut that is at the same angle as the first chamfer cut. Wall 60 has an outwardly facing surface 61 to guide a cutting tool. Outwardly facing surface 61 may be used, for example, to make distal and posterior cuts on a femur.

Figure 8:
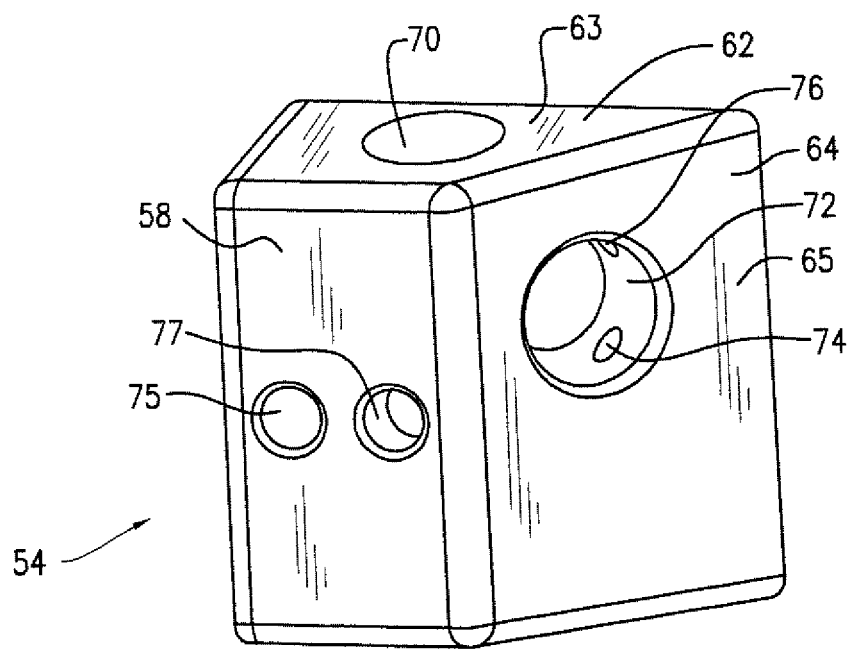
FIG. 8 is an isometric view of another embodiment of a cutting block.
Figure 9:
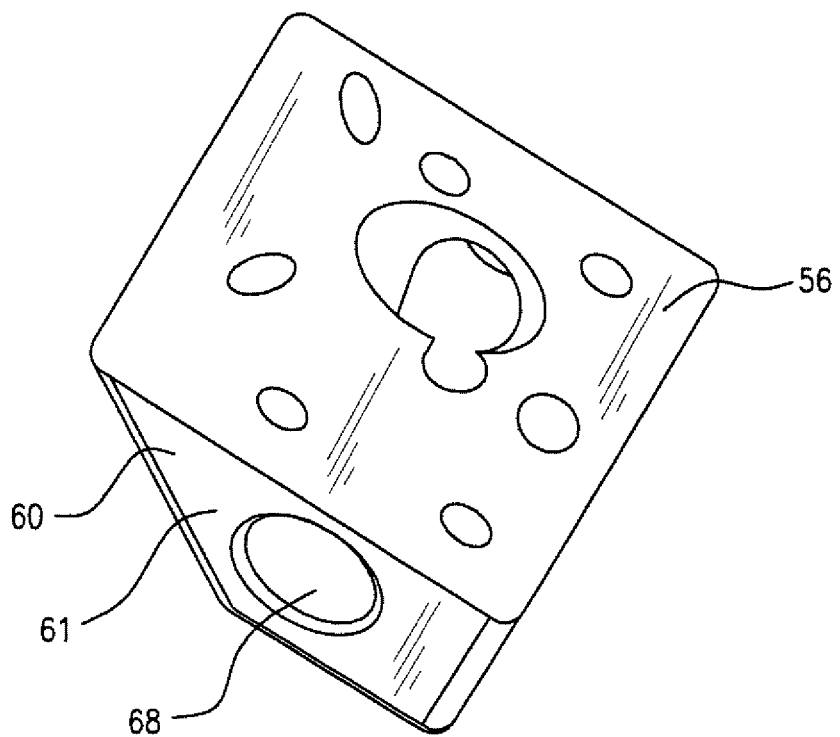
FIG. 9 is an isometric view of the cutting block of FIG. 8 from a different angle.
Figure 12:
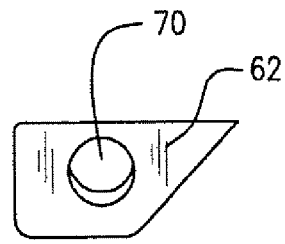
FIGS. 11, 12 and 13 are side views from different sides of the cutting block of FIG. 8.
Figures 10, 13:
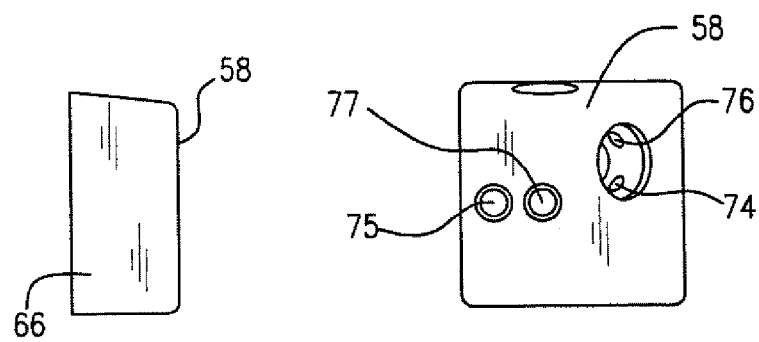
FIG. 10 is a plan view of the cutting block of FIG. 8.
Figure 11:
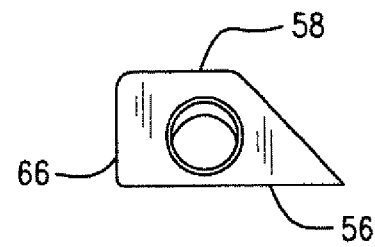
Figure 14:
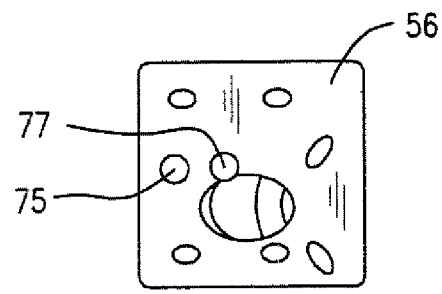
FIG. 14 is another plan view showing the base of the cutting block of FIG. 8.
Figure 15:
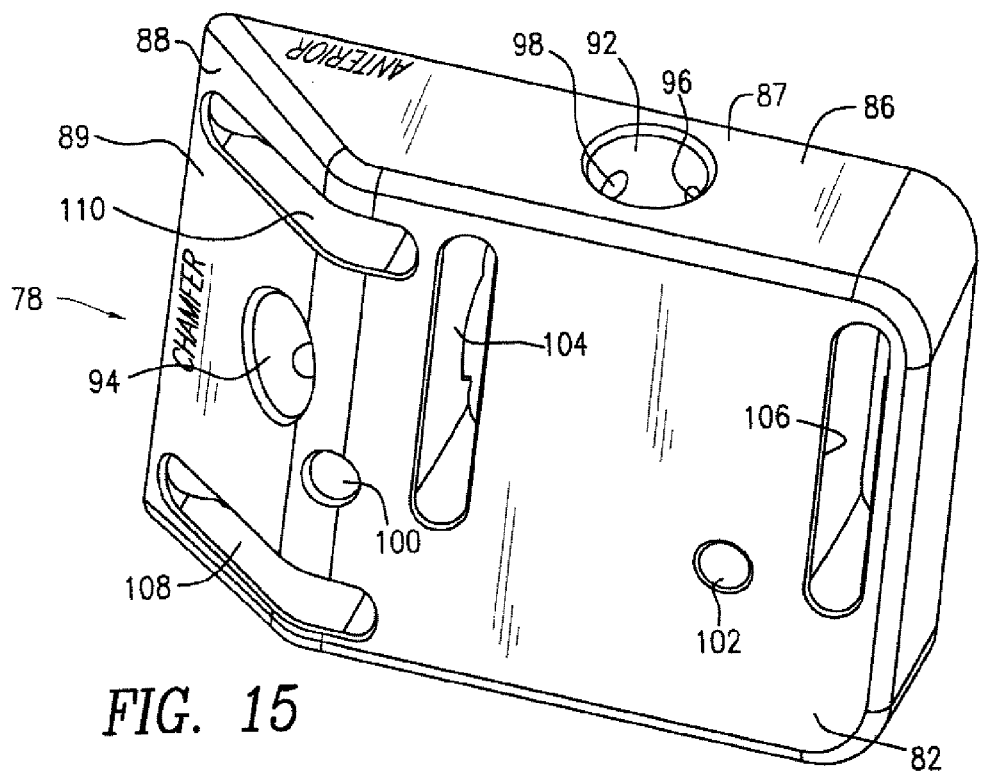
FIG. 15 is an isometric view of another embodiment of a cutting block.
Figure 16:
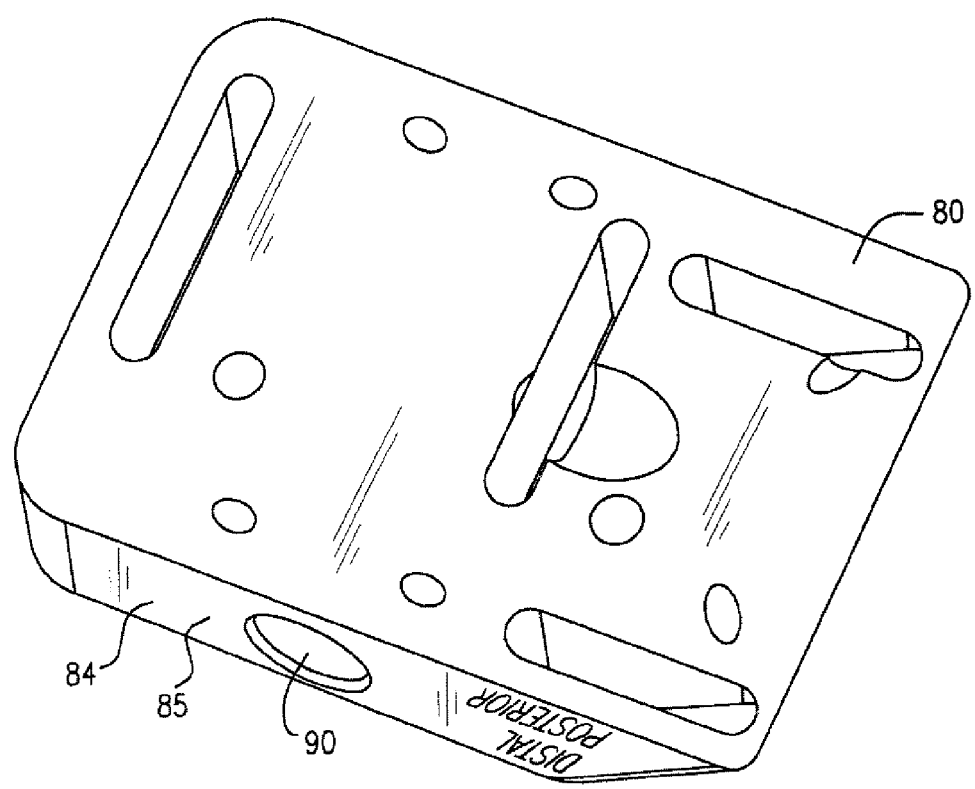
FIG. 16 is an isometric view of the cutting block of FIG. 14 from a different angle.
Figure 19:
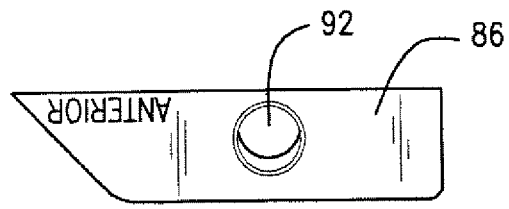
FIGS. 18, 19 and 20 are side views from different sides of the cutting block of FIG. 14.
Figures 17, 20:
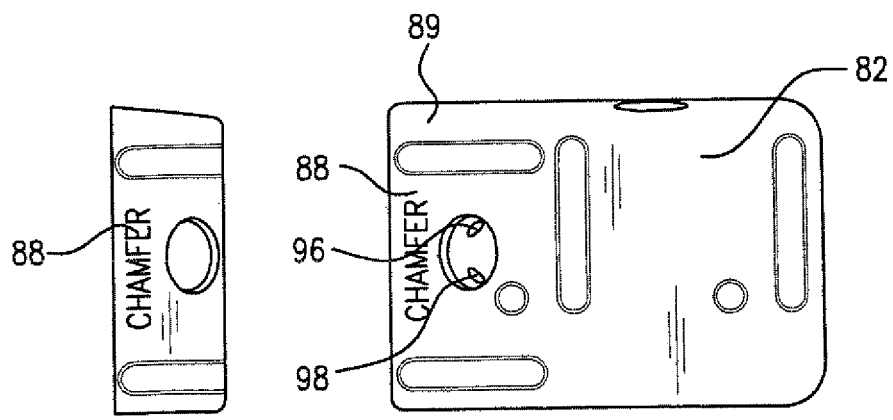
FIG. 17 is a plan view of the cutting block of FIG. 14.
Figure 18:
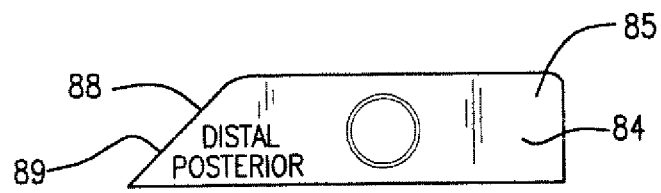
Figure 21:
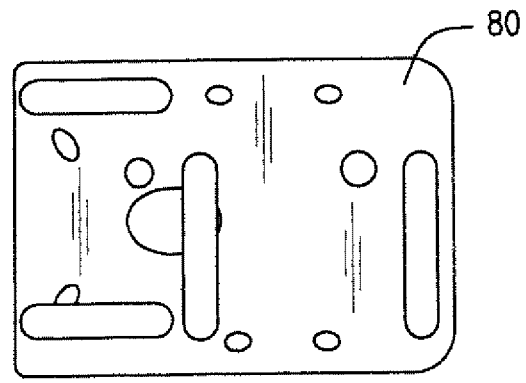
FIG. 21 is another plan view showing the base of the cutting block of FIG. 14.
Figure 22A:
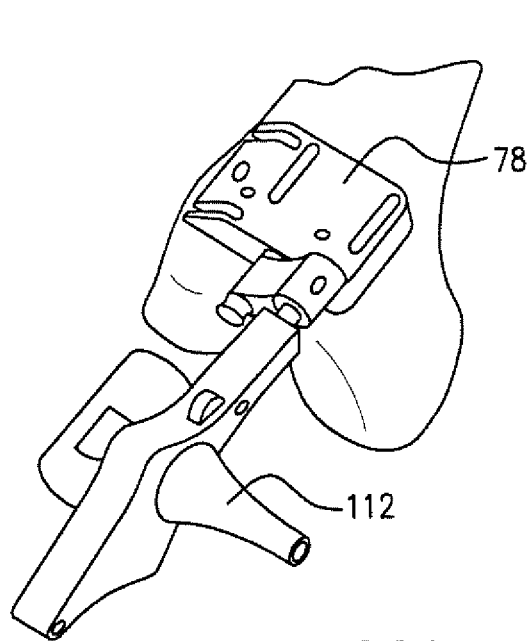
FIG. 22A shows cutting block and tracker placed on a femur for making a distal cut.
Figure 22B:
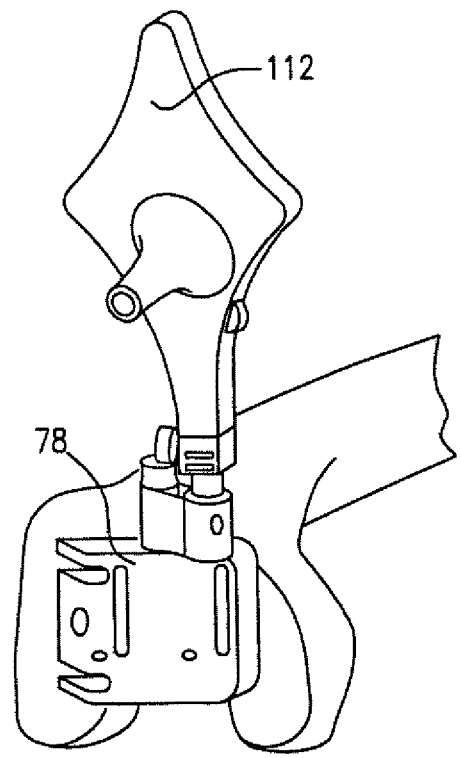
FIG. 22B shows cutting block and tracker placed on a femur for making an anterior cut.
Figure 22C:
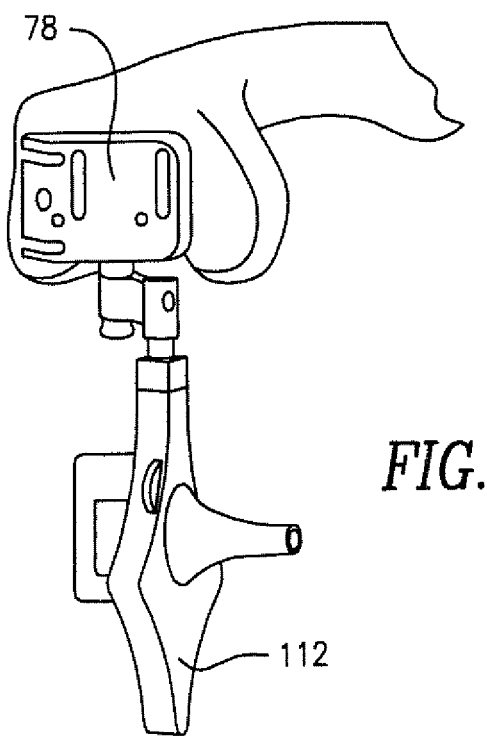
FIG. 22C shows cutting block and tracker placed on a femur for making a posterior cut.
Figure 22D:
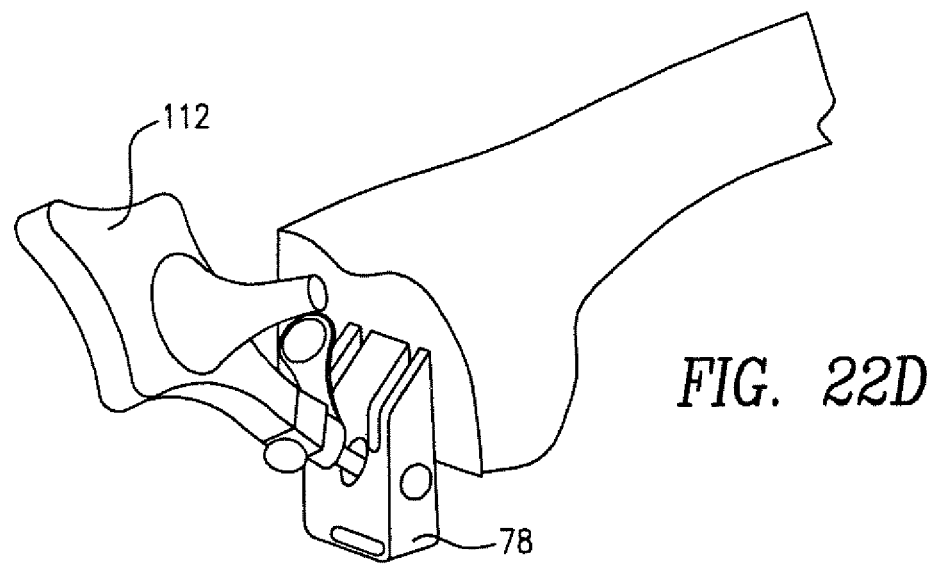
FIG. 22D shows cutting block and tracker placed on a femur for making an anterior chamfer cut.
Figure 22E:
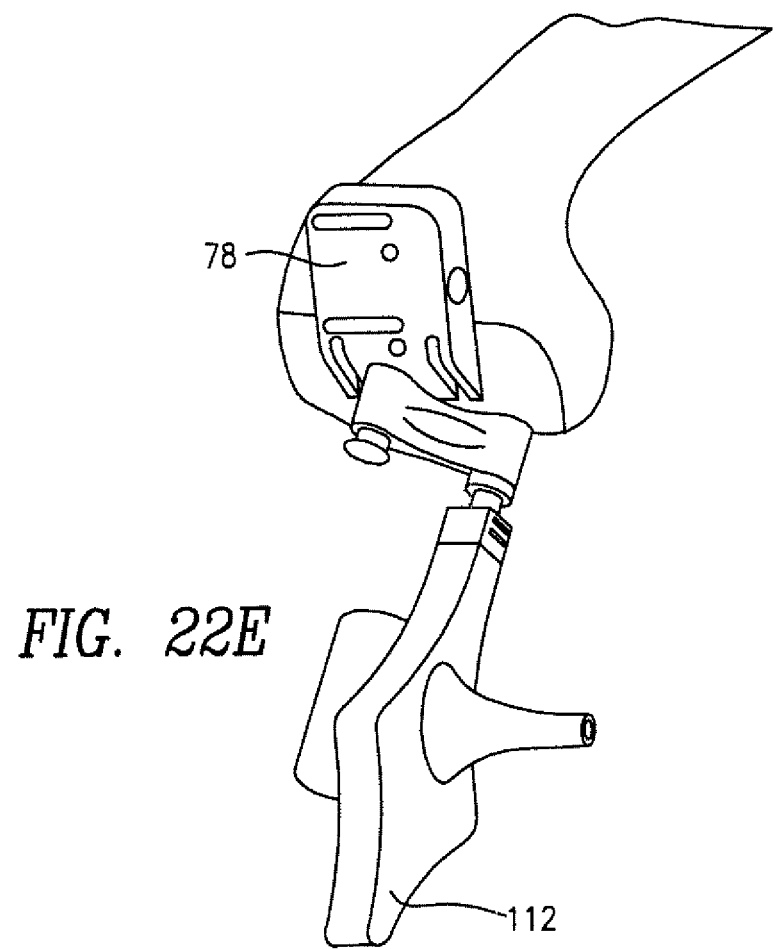
FIG. 22E shows cutting block and tracker placed on a femur for making a posterior chamfer cut.

Walls 60, 62 and 64 have attachment holes 68, 70 and 72 respectively. A tracker may be attached to any one of the attachment holes 68, 70 and 72. Attachment means of another shape or design, for example, an opening of non-circular shape or a projection or a mechanical detail of suitable geometry and construction may also be used for attaching a tracker. Holes 68, 70 and 72 each have small openings 74, 76 as seen in FIGS. 8 and 10. Openings 74 and 76 accommodate spring loaded ball like structures on the tracker attached in holes 68, 70, and 72, thereby aiding in attachment of the tracker to cutting block 54. Top 58 of cutting block 54 has two holes 75 and 77. Top 58 may have more or less holes. A pin may be driven through one or more holes 75 and 77 to attach cutting block 54 to a bone.

FIGS. 15-21 show yet another embodiment of the present invention—cutting block 78. Cutting block 78 has a base 80 and a top 82. Walls 84, 86 and 88 extend from base 80 to top 82. Wall 84 has an outwardly facing surface 85 that can guide a cutting tool. The outwardly facing surface 85 may be used, for example, to make the distal and the posterior cut on a femur. Wall 86 has an outwardly facing surface 87 that can guide a cutting tool for making, for example, an anterior cut on a femur. The outwardly facing surface 87 of wall 86 may be at an angle, for example, seven degrees with respect to base 80. This angle may match the corresponding angle on the prosthesis to be used. Wall 88 has an outwardly facing surface 89 that can guide cutting tools for making, for example, chamfer cuts on a femur. The outwardly facing surface 89 forms an angle with base 80. This angle may correspond with the angle of the chamfer cut on a femur.

Walls 84, 86 and 88 have attachment holes 90, 92 and 94. Each attachment hole 90, 92, or 94 has small openings 96 and 98. The attachment of a tracker 112 to cutting block 78 is similar to the attachment of tracker to cutting block 54 and was described in detail previously in context of cutting block 54. Cutting block 78 has two holes 100 and 102. A pin 114 may be driven through one or both of holes 100 and 102 to attach cutting block 78 to a bone. Cutting block 78 has two parallel slots 104 and 106 that run in directions generally orthogonal to the outwardly facing surface 87. Cutting block 78 has a second pair of parallel slots 108 and 110 that run in direction generally orthogonal to slots 104 and 106.

FIGS. 22A-22E show cutting block 78 with tracker 112 attached to it via attachment holes 90, 92 or 94. Tracker 112 is used to position cutting block 78 on different surfaces of a femur for making various cuts. However, tracker 112 can be attached to cutting block 78 via alternate means. The alternate methods may not permit obtaining accurate positional information on all 6 degrees-of-freedom, but there may be times during a surgical procedure where 6 degree-of-freedom positional information is not required. Some instruments have recesses intended for a purpose other than attachment of a tracker; however, these recesses can also be used to locate a tracker. For example, a slotted cutting block with a recess intended to guide a saw blade can be used to locate a tracker relative to the cutting block through the use of an adaptor that has both a feature approximately the same thickness as the saw blade and that can fit in the recess and a feature that can be utilized to attach the tracker to the adaptor. Some instruments have surfaces intended for a purpose other than tracker attachment; however, these surfaces can also be used to locate a tracker. For example, an open-face cutting block, such as cutting block 78, with a surface intended to guide a saw blade can be used to locate a tracker, such as tracker 112, relative to the cutting block through the use of an adaptor (not shown) that has both a feature that can be placed in direct apposition to the surface and a feature that can be utilized to attach the tracker to the adaptor.

In use, for example, in a surgery to implant a tricompartmental (i.e., a component for replacing the medial and lateral condyler and the patellar groove on either the left or right femur) femoral component on the distal femur, cutting block 20, 54 or 78 is located on the anterior surface of a femur using navigation. To this end, the tracker pins are inserted into the bone and anatomical landmarks digitized. Tracker 112 is attached to hole 34, 68 or 90 and block 20, 54 or 78 is floated (i.e., placed free hand) onto the femur in correct orientation. In this position the outwardly facing surface 27, 61 or 85 is in correct position to resect the distal condyler surface of the femur. At this time block 20, 54 or 78 is pinned down on the femur by driving pins through a pair of holes on top 24, 58 or 82 respectively. Holes 46, 52 (or 48, 50) may be used when cutting block 20 is being used. Holes 75 and 77 are used when cutting block 54 is employed. And, in case cutting block 78 is being used, pins may be driven through holes 100 and 102. Once cutting block 20, 54 or 82 is pinned into place, the distal condyle is resected using outwardly facing surfaces 27, 61 or 85 respectively.

After distal resection, cutting block 20 is rotated and placed on the distal resected end of the femur so that base 22 rests on the resected distal surface. Cutting block 20 is placed free hand onto the femur in correct orientation. In this orientation the anterior cutting surface (i.e., the outwardly facing surface 29) is in the appropriate anterior-posterior location and the internal/external rotation of the block matches that of the transepicondylar axis, anterior-posterior axis or the orientation the surgeon sets using the navigation system. Now cutting block 20 is pinned into place by driving pins through at least two of four the holes 46, 48, 50 and 52. Next anterior resection is performed using the outwardly facing surface 29 as a guide for a cutting tool. Next, cutting block 20 is removed from the bone and tracker attached in hole 34. Cutting block 20 is placed in the correct orientation for the posterior cut, pinned to the distal end as previously described, tracker removed, and posterior cut made using the outwardly facing surface 27 as a guide for the cutting tool. Next, cutting block 20 is removed from bone, a tracker attached to hole 40, cutting block 20 is placed in the correct orientation for a chamfer cut and pinned to the bone as previously described, tracker removed and a chamfer cut made using outwardly facing surface 33. A second chamfer cut may be made in a manner similar to the first chamfer cut described above. For second chamfer cut the surgeon may be able to choose between outwardly lying surface 31 or 33 if the prosthesis has two identical chamfer angles. If the prosthesis has differing chamfer angles, one cut may be made using each one of surfaces 31 and 33.

When cutting block 78 is used, the procedure for making the distal cut and the anterior cut is same as described in the context of cutting block 20. In case of cutting block 78 holes 100 and 102 are used to pin the block to the bone for making the distal and the anterior cuts using outwardly facing surfaces 85 and 87 respectively. Thereafter, the block is removed from the bone but the pins 116 and 118 are left in place for the anterior resection. Since pins 116 and 118 are used to position cutting block 78 for the remaining resection, the rotation of the remaining resections is mechanically set and need not be navigated. Next, pins 116 and 118 are inserted in slots 104 and 106 and the cutting block 78 is slid along the pins to correct location for making the posterior cut. A tracker may be attached to hole 90 to navigate the block for posterior cut. Once correctly located, cutting block 78 is pinned in place by driving at least one pin 114 through one of the holes 100 and 102. Now the posterior resection is performed using the outwardly facing surface 87 as a guide for the cutting tool.

Next, cutting block 78 is removed, leaving pins 116 and 118 that were engaged in slots 104 and 106 in place. Cutting block 78 is rotated and pins 116 and 118 that were left in the place are inserted in slots 108 and 110. Cutting block 78 is slid along pins 116 and 118 to correct location for making a chamfer cut. A tracker may be attached to hole 94 to navigate the block for chamfer cut. Once correctly located, cutting block 78 is pinned in place by driving at least one pin 114 though holes 100 and 102. Now the anterior or posterior chamfer cut is made. Next, the process is repeated with the block rotated by 180 degrees to make the second chamfer cut.

When cutting block 54 is used, the procedure for making the distal cut and the anterior cut is same as described in the context of cutting block 20. In case of cutting block 54, holes 75 and 77 are used to pin block 54 to the bone. The distal and anterior cuts are made using the outwardly facing surfaces 61 and 63 respectively. Thereafter, the cutting block 78 is removed from the distal surface, the tracker attached to hole 68, the cutting block 78 floated into correct orientation and position for making the posterior cut, pinned in place by driving pins through holes 75 and 77 and the posterior cut made using the outwardly facing surface 61.

Next, cutting block 54 is removed from the bone, a tracker attached to hole 72 and cutting block 54 floated in correct orientation and position for making a chamfer cut. Cutting block 54 is pinned to the bone as described previously and the chamfer cut is made using the outwardly facing surface 65. Next the cutting block 54 is removed from the bone, tracker reattached to hole 72 and the process repeated with cutting block 54 rotated 180 degrees. Cutting block 54 is floated in correct orientation and position for making a second chamfer cut, it is pinned to the bone and chamfer cut is made using the outwardly facing surface 65.

Cutting block 20, 54 or 78 may also be used, for example, for resection of tibia and talus to install ankle prosthesis. The ankle may be approached from the lateral side, the fibula moved to allow access to the ankle joint and the prosthesis installed after bone resection. Cutting block 20, 54, or 78 may floated on the talus and three cuts—a distal cut and two chamfer cuts can be made. In contrast to the traditional cutting block that require different sizes, the same cutting block 20, 54 or 78 can be used for any size bone (such as a talus or a femur) since the cutting surfaces are referenced to each other in terms of angular relationship but not linear relationship which is set by the navigation system.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A method of resecting bone, the method comprising the steps of:
   providing a cutting block adapted to resect the bone for installation of a prosthetic device;
   locating the cutting block on the bone using a navigation system;
   making a cut on the bone using a surface of the cutting block to guide a cutting instrument resulting in a resected surface;
   locating the cutting block in a first position on the resected surface using the navigation system;
   anchoring the cutting block on the resected surface using pins; and
   using the pins installed for anchoring in the first position to mechanically fix the rotation of the cutting block in subsequent positions for resecting the bone, wherein movement of the cutting block between each of the subsequent positions includes temporarily removing the cutting block from the resected surface.

2. A method of resecting a femur, the method comprising the steps of:
   locating a cutting block on an anterior surface of the femur using a navigation system;
   making a distal cut on the femur using a surface of the cutting block to guide a cutting instrument, the cutting block being located on the anterior surface of the femur, and the distal cut resulting in a planer distal surface;
   locating the cutting block in a first position on the planer distal surface using the navigation system;
   anchoring the cutting block on the planer distal surface using pins;
   re-locating the cutting block to each of second, third and fourth positions on and with respect to the planer distal surface using the navigation system;
   making an anterior cut, a posterior cut, an anterior chamfer cut and a posterior chamfer cut each using a surface of the cutting block as a guide, the cutting block being anchored in the first, second, third and fourth positions during the making of the anterior cut, the posterior cut, the anterior chamfer cut, and the posterior chamfer cut, respectively.

3. The method of claim 2, further comprising the steps of:
   using the pins installed for anchoring in the first position to mechanically fix the rotation of the relocated cutting block in the second, third, and fourth positions.

4. The method of claim 2, further comprising the step of:
   providing the cutting block adapted to resect the femur for installation of a prosthetic device, the cutting block having an angled surface, an angle of the angled surface matching an angle on the prosthetic device.

5. The method of claim 2, wherein the cutting block is removed from the planer distal surface during each step of re-locating the cutting block in the second, third, and fourth positions.

6. A method of resecting a femur, the method comprising the steps of:
   locating a cutting block on an anterior surface of the femur using a navigation system;
   making a distal cut on the femur using a surface of the cutting block to guide a cutting instrument, the cutting block being located on the anterior surface of the femur, and the distal cut resulting in a planer distal surface;
   locating and anchoring the cutting block in a first position on the planer distal surface using the navigation system;
   making a first cut that is one of an anterior cut, a posterior cut, an anterior chamfer cut and a posterior chamfer cut using a surface of the cutting block as a guide;
   removing the cutting block from the first position on the planer distal surface;
   locating and anchoring the cutting block in a second position different from the first position on the planer distal surface using the navigation system;
   making a second cut that is a different one of an anterior cut, a posterior cut, an anterior chamfer cut and a posterior chamfer cut using a surface of the cutting block as a guide;
   removing the cutting block from the second position on the planer distal surface;
   locating and anchoring the cutting block in a third position different from the first and second positions on the planer distal surface; and
   making a third cut different from the first and second cuts that is a different one of an anterior cut, a posterior cut, an anterior chamfer cut and a posterior chamfer cut using a surface of the cutting block as a guide.

7. The method of claim 6, wherein the steps of anchoring include anchoring the cutting block on the planer distal surface using pins.

* * * * *